United States Patent
Inoue (10) Patent No.: US 7,899,157 B2
(45) Date of Patent: Mar. 1, 2011

(54) X-RAY IMAGE DIAGNOSIS APPARATUS AND CONTROL METHOD THEREFOR

(75) Inventor: Chizuru Inoue, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 65 days.

(21) Appl. No.: 12/476,801

(22) Filed: Jun. 2, 2009

(65) Prior Publication Data

US 2009/0310750 A1    Dec. 17, 2009

(30) Foreign Application Priority Data

Jun. 13, 2008    (JP)    ............... 2008-155886

(51) Int. Cl.
   *H05G 1/58*    (2006.01)
(52) U.S. Cl. ..................................... 378/116
(58) Field of Classification Search ............ 378/4, 378/19, 114, 116, 64, 65
   See application file for complete search history.

(56) References Cited

U.S. PATENT DOCUMENTS

| | | | | |
|---|---|---|---|---|
| 5,054,044 A | * | 10/1991 | Audon et al. | 378/91 |
| 7,130,377 B2 | * | 10/2006 | Matsuno | 378/96 |
| 2007/0230661 A1 | * | 10/2007 | Motoki et al. | 378/116 |

FOREIGN PATENT DOCUMENTS

JP    2927206    5/1999

* cited by examiner

*Primary Examiner*—Irakli Kiknadze
(74) *Attorney, Agent, or Firm*—Fitzpatrick, Cella, Harper & Scinto (57) ABSTRACT

A CPU (201) acquires objective information indicating the objective of X-ray photography before X-ray photography is performed, and sets an X-ray photography mode corresponding to the acquired objective information. After the start of X-ray photography, the CPU then determines whether information communication from an operation unit (110) is normal. Upon determining that information communication is not normal, the CPU performs operation control on X-ray photography in accordance with the set X-ray photography mode.

4 Claims, 8 Drawing Sheets

| OBJECTIVE OF PHOTOGRAPHY | OPERATION MODE |
|---|---|
| SURGICAL OPERATION A | (FIRST MODE)<br>PHOTOGRAPHY UNDER IRRADIATION CONDITIONS SET IMMEDIATELY BEFORE OCCURRENCE OF ABNORMALITY IN COMMUNICATION OF OPERATION INSTRUCTION INFORMATION |
| SURGICAL OPERATION B, SURGICAL OPERATION C | (SECOND MODE)<br>PHOTOGRAPHY UNDER PREDETERMINED IRRADIATION CONDITIONS SET IN ADVANCE |
| SURGICAL OPERATION D, EXAMINATION E | (THIRD MODE)<br>PHOTOGRAPHY UNDER ABC (Auto Brightness Control) CONTROL |
| EXAMINATION F | (FOURTH MODE)<br>STOPPING OF PHOTOGRAPHY |

FIG. 8

X-RAY IMAGE DIAGNOSIS APPARATUS AND CONTROL METHOD THEREFOR

BACKGROUND OF THE INVENTION

1. Field of the Invention

The present invention relates to a technique for performing X-ray photography.

2. Description of the Related Art

A conventionally existing X-ray image diagnosis apparatus includes the following components:

- an X-ray generation unit to irradiate X-rays
- an X-ray detection unit placed to face the X-ray generation unit
- a bed which is provided between the X-ray generation unit and the X-ray detection unit and on which an object is placed
- a holding unit to hold the X-ray generation unit, X-ray detection unit, and bed and change their positions
- an image processing unit to process image data read out from the X-ray detection unit
- an operation unit to input X-ray irradiation condition settings, an instruction to start irradiation, information of an object, and the like
- a system controller to perform operation control on each component described above When a doctor or technician who is an operator inputs X-ray irradiation condition settings and various kinds of operation instructions such as an instruction to start irradiation, the operation instruction information is communicated to the system controller. The system controller performs position adjustment for the X-ray generation unit, X-ray detection unit, and bed, starting and stopping of irradiation of X-rays, starting and stopping of image reading from the X-ray detection unit, and the like by sending control instructions to the respective units described above based on the above operation instruction information, thereby performing X-ray photography.

In this case, the operation unit may be placed in a medical room in which X-ray irradiation is performed or in an operation room different from the medical room. Alternatively, such operation units may be placed in both the medical room and the operation room. Such operation unit is connected to the system controller via a cable.

In general, various kinds of operation instructions are input to the X-ray image diagnosis apparatus via this operation unit. Conventionally, the X-ray image diagnosis apparatus is provided with an emergency stop button or the like in a system different from that of the operation unit. The operator presses such an emergency stop button in the event of a contingency, e.g., failure to communicate operation instruction information due to some cause such as disconnection or breakage of the cable which connects the operation unit to the system controller at the time of X-ray irradiation. That is, this button is provided for the safety of patients.

For example, patent reference 1 (Japanese Patent No. 2927206 (Japanese Patent Laid-Open No. 8-299317)) discloses a technique for monitoring a communication abnormality between devices constituting the X-ray image diagnosis apparatus. Patent reference 1 discloses an X-ray image diagnosis apparatus which includes a function of monitoring a communication abnormality between devices constituting the X-ray image diagnosis apparatus and specifying whether the abnormality resides in the cable connecting the respective devices or in each device itself.

The conventional technique, however, has the following problem. That is, when the operator cannot communicate operation instruction information associated with irradiation via the operation unit during X-ray irradiation, he/she can only perform operation like stopping irradiation by pressing the emergency stop button provided in a different system.

In addition, if the operator cannot communicate operation instruction information associated with irradiation, he/she cannot change any X-ray irradiation conditions. Irradiation is therefore continued under the irradiation conditions set immediately before the failure to communicate information. This poses a serious problem when X-ray photography must be continued during a surgical operation. If, for example, a failure to communicate operation instruction information occurs while a high dose of X-ray irradiation is temporarily set, photography is continued under the high dose of X-ray irradiation. This may irradiate the patient with an excessive dose of X-rays.

SUMMARY OF THE INVENTION

The present invention has been made in consideration of the above problem, and provides a technique for controlling X-ray photography in accordance with the objective of X-ray photography even if it becomes impossible to communicate operation instruction information from an operation unit.

According to the first aspect of the present invention, an X-ray image diagnosis apparatus comprising an operation unit configured to input an instruction concerning X-ray photography, an X-ray photography unit configured to perform X-ray photography, and a controller configured to perform operation control on the X-ray photography unit based on control information input by the operation unit, the controller comprising a unit configured to acquire objective information indicating an objective of performing X-ray photography before X-ray photography is performed, a setting unit configured to set an X-ray photography mode corresponding to the objective information, a determination unit configured to determine whether information communication from the operation unit is normal, after the X-ray photography unit starts X-ray photography, and a control unit configured to perform operation control on the X-ray photography unit in accordance with an X-ray photography mode set by the setting unit, when the determination unit determines that the information communication is not normal.

According to the second aspect of the present invention, a control method for an X-ray image diagnosis apparatus including an operation unit configured to input an instruction concerning X-ray photography, an X-ray photography unit configured to perform X-ray photography, and a controller configured to perform operation control on the X-ray photography unit based on control information input by the operation unit, wherein the controller performs a step of acquiring objective information indicating an objective of performing X-ray photography before X-ray photography is performed, a setting step of setting an X-ray photography mode corresponding to the objective information, a determination step of determining whether information communication from the operation unit is normal, after the X-ray photography unit starts X-ray photography, and a control step of performing operation control on the X-ray photography unit in accordance with an X-ray photography mode set in the setting step, when it is determined in the determination step that the information communication is not normal.

Further features of the present invention will become apparent from the following description of exemplary embodiments with reference to the attached drawings.

DESCRIPTION OF THE EMBODIMENTS

Preferred embodiments of the present invention will be described in detail below with reference to the accompanying drawings. Note that these embodiments will be described as examples of the preferred arrangements of the present invention described in the scope of the appended claims. The present invention is not limited to the embodiments described below.

First Embodiment

Figure 1:
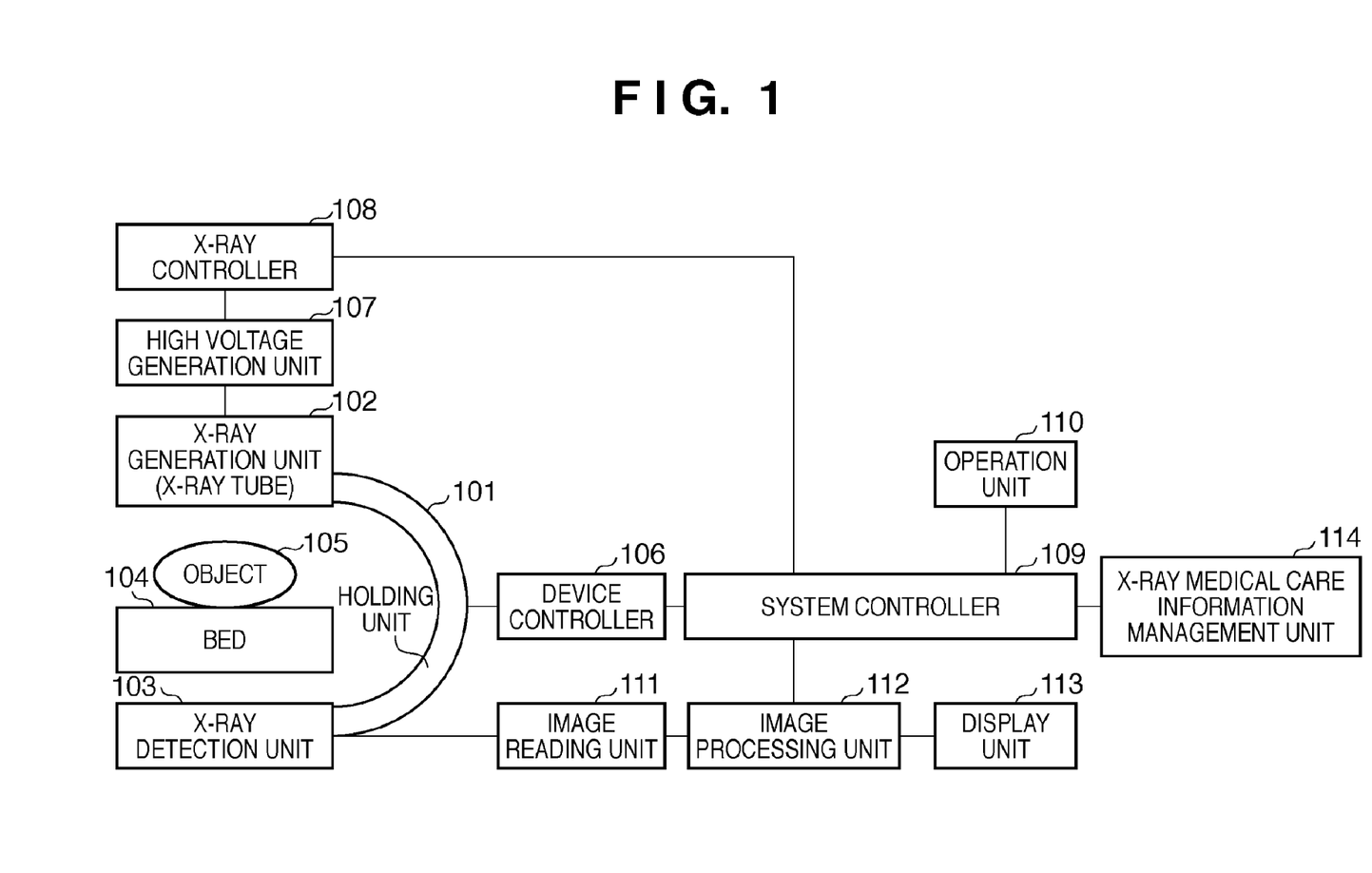
FIG. 1 is a block diagram showing an example of the functional arrangement of an X-ray image diagnosis apparatus according to the first embodiment of the present invention.

FIG. 1 is a block diagram showing an example of the functional arrangement of an X-ray image diagnosis apparatus according to this embodiment.

A holding unit 101 has an X-ray generation unit (X-ray tube) 102 as an X-ray source on one end, and an X-ray detection unit 103 for detecting X-rays transmitted through an object 105 on the other end. That is, the holding unit 101 serves to fix/hold the X-ray generation unit 102 and the X-ray detection unit 103 while they face each other.

A bed 104 is provided between the X-ray generation unit 102 and the X-ray detection unit 103. The bed 104 includes a top panel (not shown) and leg portions (not shown) which support the top panel. The object 105 as a patient is placed on the top panel.

The top panel is configured to be movable in required directions, e.g., the vertical and horizontal directions. The top panel (not shown) of the bed 104 and the holding unit 101 are each provided with a motor (not shown) and a position sensor (not shown). Each motor and each position sensor are connected to a device controller 106. The device controller 106 drives/controls each motor in accordance with sensor information obtained by the position sensor. This drives/controls the top panel of the bed 104 and the holding unit 101 so as to establish a required positional relationship.

The X-ray generation unit 102 is connected to a high voltage generation unit 107. Upon receiving a required voltage from the high voltage generation unit 107, the X-ray generation unit 102 irradiates the object 105 with X-rays. The high voltage generation unit 107 is connected to an X-ray controller 108. The X-ray controller 108 serves to drive/control the high voltage generation unit 107. Upon receiving such driving control, the high voltage generation unit 107 controls, for example, the amount of X-rays (voltage in reality) irradiated from the X-ray generation unit 102 when performing X-ray photography (static image radiograph and moving image capturing).

The device controller 106 and the X-ray controller 108 are connected to the system controller 109.

An image reading unit 111 is connected to the X-ray detection unit 103. Upon detecting X-rays irradiated from the X-ray generation unit 102 and transmitted through the object 105 and the bed 104, the X-ray detection unit 103 forms image data (X-ray image data) based on the amount of X-rays detected. Since the processing of forming X-ray image data by the X-ray detection unit 103 is a known technique, a repetitive description will be omitted.

The image reading unit 111 reads the image data formed by the X-ray detection unit 103 from the X-ray detection unit 103, and transmits the read image data to an image processing unit 112 on the subsequent stage.

The image processing unit 112 performs image processing such as gamma correction and noise removal for the image data received from the image reading unit 111. The image processing unit 112 then generates a video signal by superimposing, on the image data having undergone such image processing, other information received from the system controller 109, and transmits the generated signal to a display unit 113 on the subsequent stage. The other information received from the system controller 109 includes information of the object 105 (a name, an age, a sex, a height, a weight, a target region subjected to static image radiography or moving image capturing, and the like) and static image radiography and moving image capturing conditions including X-ray irradiation conditions.

The display unit 113 includes a CRT or a liquid crystal screen, and displays a video based on the signal transmitted from the image processing unit 112.

The system controller 109 performs operation control on each process to be described as being performed by the X-ray image diagnosis apparatus by performing operation control on each of the device controller 106, the X-ray controller 108, the image reading unit 111, the image processing unit 112, an operation unit 110, and an X-ray medical care information management unit 114.

The operation unit 110 serves to input various kinds of instructions to the system controller 109. The operation unit 110 includes, for example, a keyboard, mouse, touch panel, membrane button, and joystick which are used to input X-ray irradiation conditions, information of the object 105, and the like. The operation unit 110 also includes an irradiation switch and foot pedal which give triggers to start and stop irradiation.

Upon receiving static image radiography or moving image capturing conditions, object information (a name, an age, a sex, a height, a weight, a target region subjected to static image radiograph or moving image capturing, and the like), technician information, and the like from the operation unit 110, the system controller 109 transmits them as the above "other information" to the image processing unit 112. Obviously, there is no need to transmit all these pieces of information at once, and it suffices to transmit only information corresponding to an instruction from the operation unit 110 as needed.

In addition, pieces of information such as photography conditions are transmitted to the X-ray controller 108, device controller 106, and image reading unit 111.

The system controller 109 also controls the read start timing of the image reading unit 111 via the image processing unit 112.

The X-ray medical care information management unit 114 manages the medical care information of patients within a hospital. For example, the X-ray medical care information management unit 114 manages the names, ages, sexes, heights, and weights of patients, doctors in attendance, treatment plans, information of examinations and surgical operations using X-ray irradiations (reservation information, reception information, images obtained by still image radiography and moving image capturing, and the like), target regions subjected to still image radiography or moving image capturing, diagnosis results, and the like. In general, as a communication system for all kinds of information associated with patients within the hospital, a HIS/RIS (Hospital Information System/Radiology Information System) is known.

The system controller 109 is connected to the X-ray medical care information management unit 114, and transmits/receives in-house patient information, examination information, and surgical operation information to/from the X-ray medical care information management unit 114.

Figure 2:
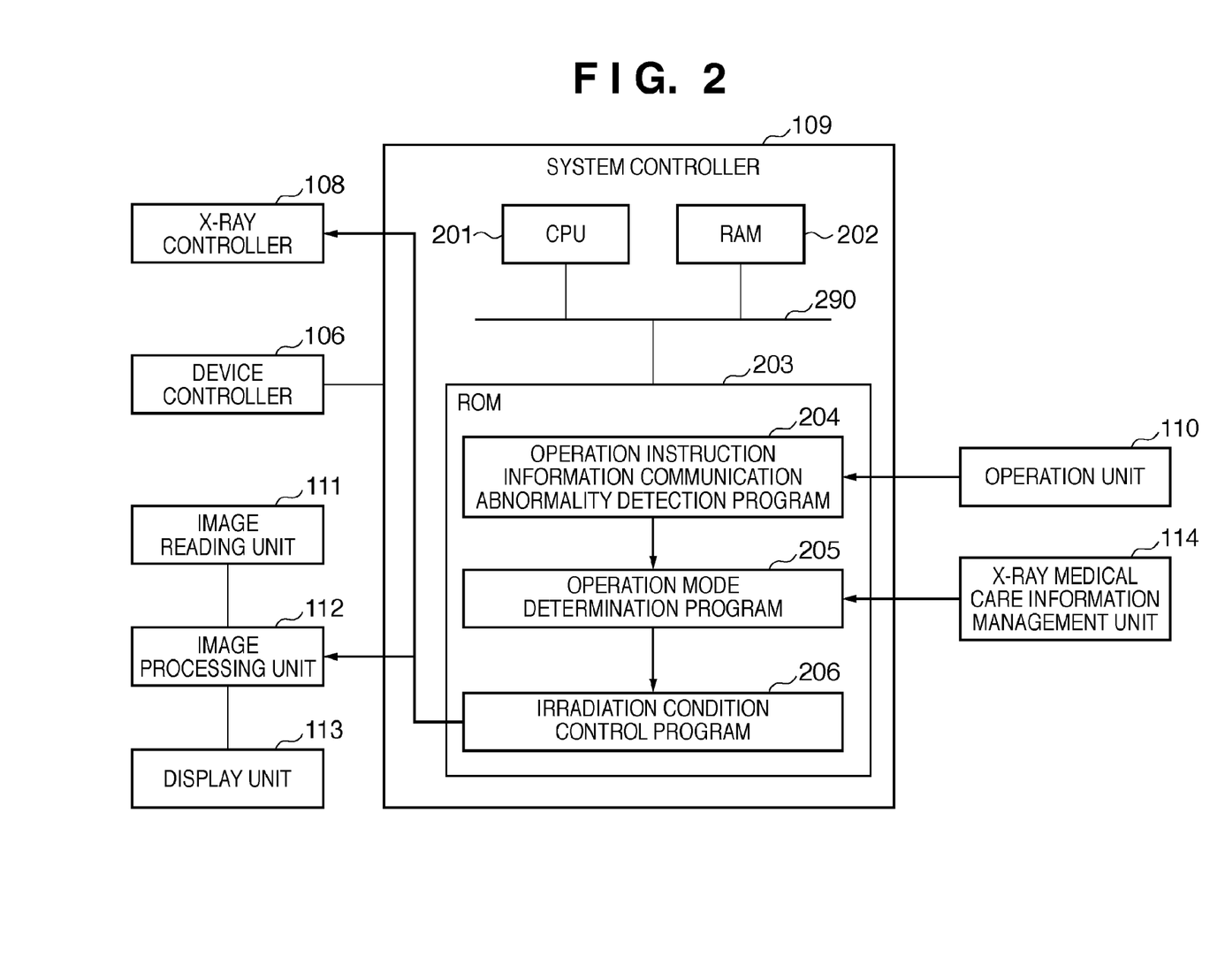
FIG. 2 is a block diagram showing an example of the arrangement of a system controller 109.

FIG. 2 is a block diagram showing an example of the arrangement of the system controller 109.

As shown in FIG. 2, the system controller 109 includes a CPU 201, a RAM 202, and a ROM 203, which are connected to a bus 290.

The CPU 201 controls the overall X-ray image diagnosis apparatus by using the programs and data stored in the ROM 203 and the data stored in the RAM 202, and performs each process to be described as being performed by the system controller 109.

The RAM 202 has an area for temporarily storing various data read out by the CPU 201 from the X-ray medical care information management unit 114, and also has a work area to be used when the CPU 201 performs various kinds of processes. That is, the RAM 202 can provide various areas, as needed.

As shown in FIG. 2, the ROM 203 stores an operation instruction information communication abnormality detection program 204, an operation mode determination program 205, and an irradiation condition control program 206. Note that in addition to these programs, the ROM 203 stores information which will appear as known information in the following description and information which is handled as known information for those skilled in the art. In addition, the ROM 203 stores basic setting data and a startup program for the X-ray image diagnosis apparatus.

The operation instruction information communication abnormality detection program 204, operation mode determination program 205, and irradiation condition control program 206 stored in the ROM 203 each will be described next.

The operation instruction information communication abnormality detection program 204 checks whether instruction information associated with X-ray photography (operation instruction information associated with X-ray irradiation) such as X-ray irradiation condition settings and instructions to start and stop irradiation from the operation unit 110 is normally communicated. The operation instruction information communication abnormality detection program 204 then notifies the operation mode determination program 205 of the result of this check.

The operation mode determination program 205 derives objective information indicating the objective of X-ray photography based on the medical care information of the object 105 to be subjected to X-ray photography, which the CPU 201 loads from the X-ray medical care information management unit 114 into the RAM 202. The medical care information includes a treatment plan and information about an examination or surgical operation using X-ray irradiation (reservation information and reception information), as described above. The operation mode determination program 205 determines an operation mode corresponding to the derived objective information among a plurality of operation modes (X-ray photography modes) which can be set in the X-ray image diagnosis apparatus. Upon being notified, from the operation instruction information communication abnormality detection program 204, of a check result indicating that information communication from the operation unit 110 is not normally performed, the operation mode determination program 205 notifies the irradiation condition control program 206 of the determined operation mode.

The irradiation condition control program 206 drives/controls the X-ray controller 108 and the image reading unit 111 based on preset information. The preset information includes pieces of irradiation condition information such as a tube current, tube voltage, and frame rate for the irradiation of X-rays, and setting information such ON/OFF of ABC (Auto Brightness Control) control. Note that the operation of the irradiation condition control program 206 to be performed when the operation mode determination program 205 notifies the irradiation condition control program 206 of the operation mode will be described later.

Note that the function of each program described above can be implemented by making the CPU 201 perform a corresponding program.

Figure 3:
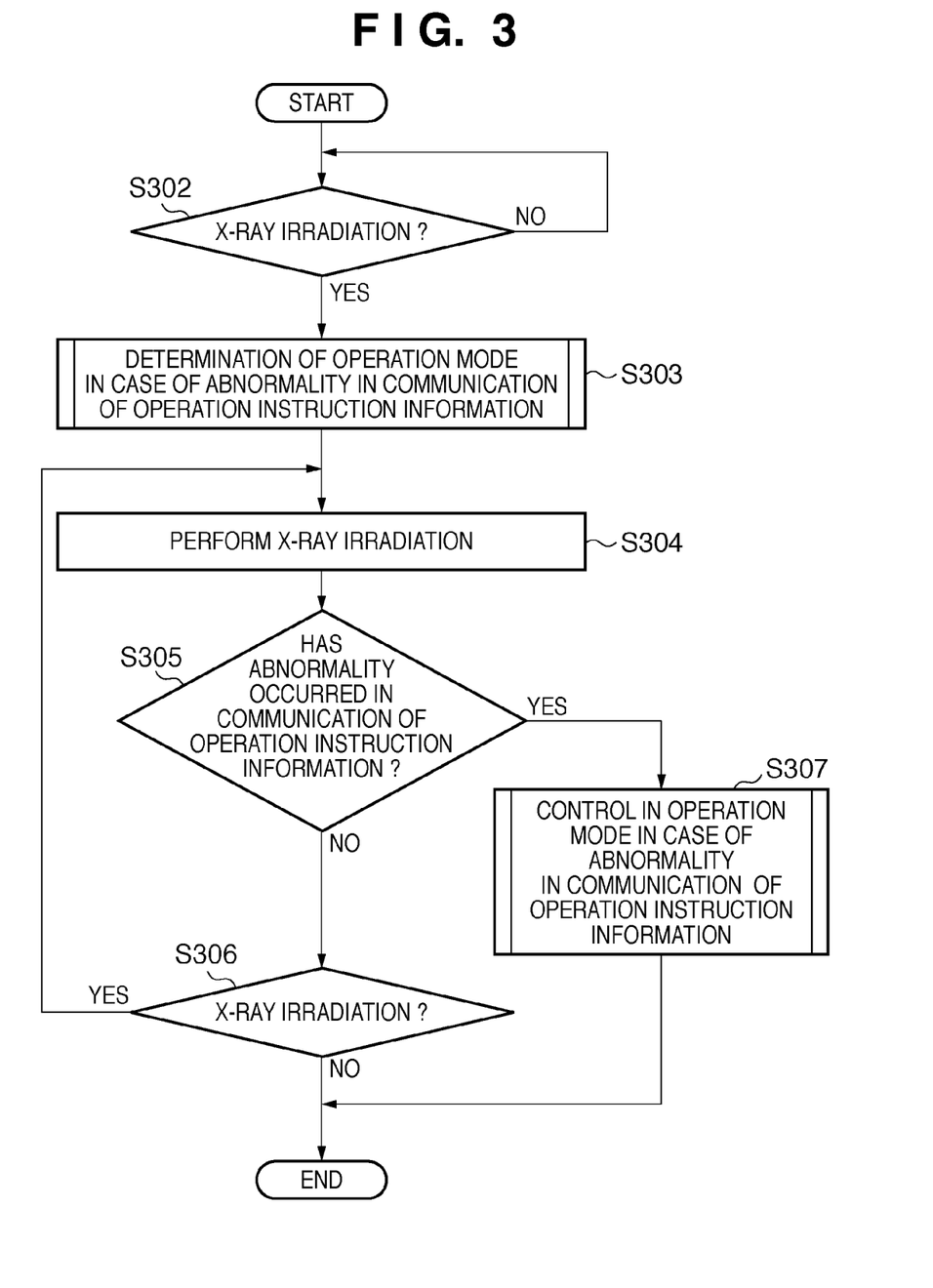
FIG. 3 is a flowchart for X-ray photography processing performed by the X-ray image diagnosis apparatus.

FIG. 3 is a flowchart for X-ray photography processing performed by the X-ray image diagnosis apparatus. Assume that when processing based on this flowchart is started, the medical care information of the object 105 has already been loaded from the X-ray medical care information management unit 114 into the RAM 202. Obviously, it suffices to load such medical information into the RAM 202 at a necessary timing.

In step S302, the CPU 201 waits for an instruction to start X-ray irradiation (X-ray photography). When such an instruction is input via the operation unit 110, the process advances to step S303. The CPU 201 waits in step S302 unless such an instruction is input. The operator issues an instruction to start X-ray irradiation by, for example, pressing a foot pedal or irradiation switch of the operation unit 110.

In step S303, the CPU 201 performs the operation mode determination program 205. With this operation, the CPU 201 derives (acquires) objective information indicating the objective of X-ray photography based on the medical care information of the object 105 which is loaded into the RAM 202 in advance. The CPU 201 then determines an operation mode corresponding to the derived objective information among the plurality of operation modes which can be set in the X-ray image diagnosis apparatus.

Figure 4:
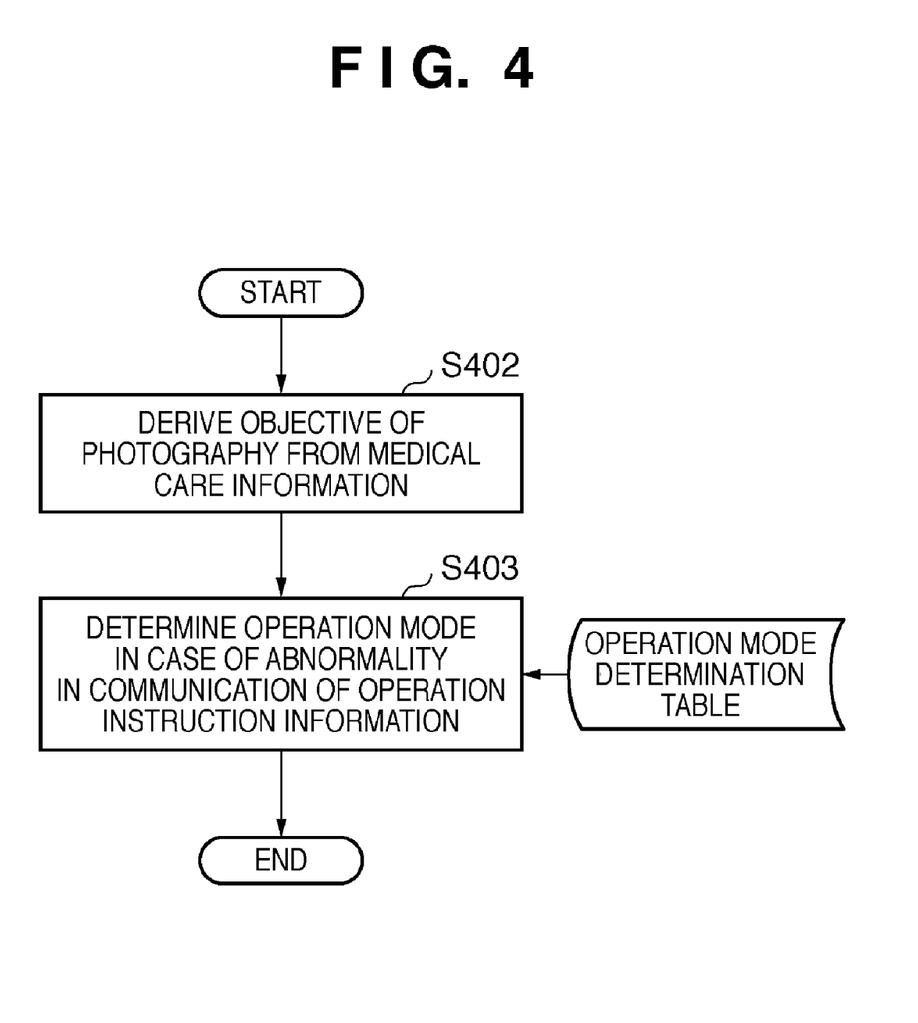
FIG. 4 is a flowchart showing the details of processing in step S303.

The details of processing in step S303 will be described later with reference to the flowchart of FIG. 4.

In step S304, the CPU 201 performs the irradiation condition control program 206. With this operation, the CPU 201 controls the X-ray controller 108 as an X-ray photography unit and the image reading unit 111 (via the image processing unit 112) based on pieces of irradiation condition information such as a tube current, tube voltage, and frame rate and setting information such as ON/OFF of ABC control. With this operation, X-ray irradiation starts. Note that the pieces of irradiation condition information and medical care information such as setting information include the default values set in advance via the operation unit 110 or the values (control information) set by a doctor or technician before a surgical operation.

In step S305, the CPU 201 performs the operation instruction information communication abnormality detection program 204. With this operation, the CPU 201 checks whether operation instruction information associated with X-ray irradiation is normally communicated from the operation unit 110.

More specifically, the CPU 201 transmits predetermined abnormality detection information to the operation unit 110 after the start of X-ray photography. If communication between the CPU 201 and the operation unit 110 is normal, since this abnormality detection information normally reaches the operation unit 110, the operation unit 110 performs predetermined processing for the abnormality detection information and returns the processed abnormality detection information to the CPU 201. The CPU 201 then checks whether this returned abnormality detection information is information having a predetermined content. If it is determined as a result of this check that the returned abnormality detection information is not information having the predetermined content or if no information is returned for a predetermined period of time or more after the abnormality detection information is transmitted to the operation unit 110, the CPU 201 determines that information communication from the operation unit 110 is not normally performed. Obviously, if it is determined as a result of this check that the returned abnormality detection information is information having the predetermined content and is returned within predetermined period of time after the abnormality detection information is transmitted to the operation unit 110, the CPU 201 determines that information communication from the operation unit 110 is normally performed.

If it is detected that an abnormality has occurred in information communication from the operation unit 110, the process advances to step S307. If no abnormality is detected, the process advances to step S306.

Note that the check processing to be performed in step S305 is not limited to the above processing, and various kinds of processing are conceivable.

In step S306, the CPU 201 checks whether an instruction to start X-ray irradiation is continued. For example, the CPU 201 checks whether the operator keeps pressing the foot pedal or irradiation switch of the operation unit 110. If it is determined as a result of this check that the instruction to start X-ray irradiation is continued, the process advances to step S304. If the instruction to start X-ray irradiation is not continued, this processing is terminated.

In step S307, the CPU 201 performs the irradiation condition control program 206. The CPU 201 controls the X-ray controller 108 based on the operation mode determined in step S303, and also controls the image reading unit 111 via the image processing unit 112. The details of processing in step S307 will be described later with reference to the flowchart shown in FIG. 6.

The details of processing in step S303 will be described next with reference to FIG. 4. FIG. 4 is a flowchart showing the details of processing in step S303.

First of all, in step S402, the CPU 201 performs the operation mode determination program 205. With this operation, the CPU 201 derives (acquires) objective information indicating the objective of X-ray photography based on the medical care information of the object 105. The processing in this step will be described in detail later.

Subsequently, in step S403, the CPU 201 refers to the table (operation mode determination table) exemplified in FIG. 5 first. The CPU 201 then determines an operation mode corresponding to the objective information derived in step S402.

Figure 5:
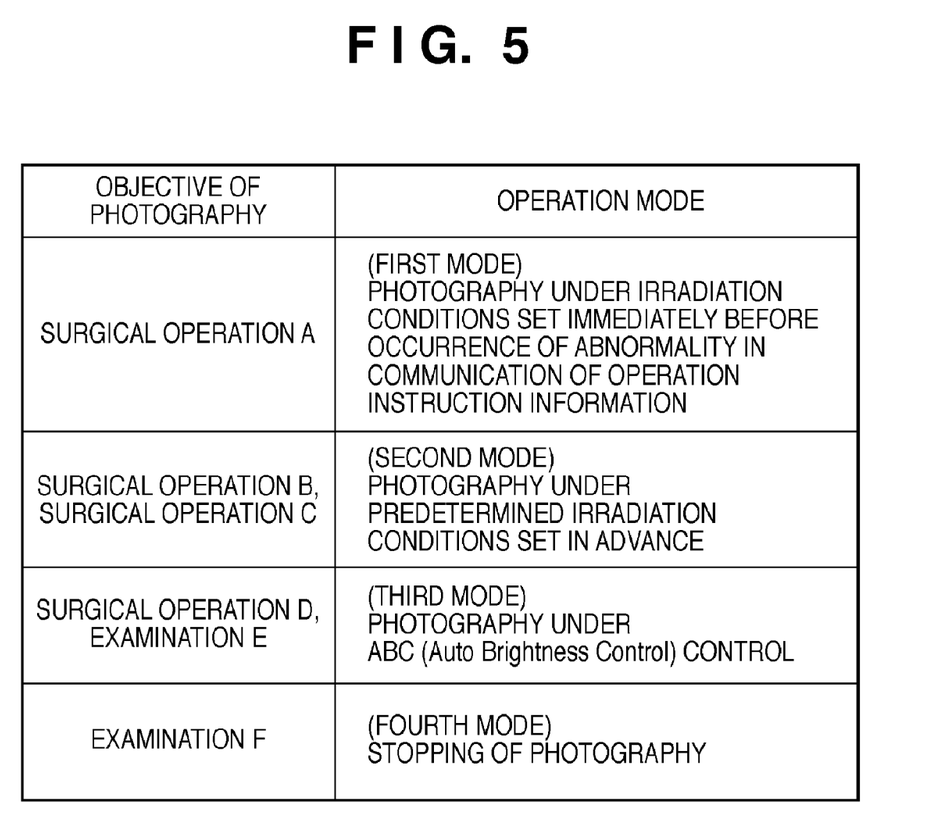
FIG. 5 is a view showing an example of the arrangement of a table indicating the correspondence relationship between objective information and operation modes.

FIG. 5 is a view showing an example of the arrangement of a table indicating the correspondence relationship between objective information and operation modes. Assume that the data of the table exemplified in FIG. 5 is generated in advance and stored in the ROM 203.

In this embodiment, it is possible to select one of a plurality of operation modes and set it in the X-ray image diagnosis apparatus. A specific one of the plurality of operation modes is determined in accordance with the objective of X-ray photography to be performed. In this embodiment, therefore, an operation mode corresponding to the objective information derived in step S402 is determined by using the table in FIG. 5.

In the table exemplified in FIG. 5, four modes, namely the first, second, third, and fourth modes, and objective information corresponding to each mode are registered.

If, for example, the objective of X-ray photography to be performed is "surgical operation A", i.e., if the objective information derived in step S402 indicates "surgical operation A", the first mode is selected in step S403. The first mode is a mode for keeping operation control on the X-ray controller 108 and the image reading unit 111, which has been performed immediately before it is determined that information communication from the operation unit 110 is not normally performed, after such determination. The first mode is an operation mode which attaches importance to the availability of the apparatus when, for example, the risk produced by the interruption of irradiation is high.

Assume that brain surgery is performed while X-ray photography is performed. In this case, interrupting X-ray photography will produce a high risk. In addition, since special photography conditions are often set for X-ray photography performed during brain surgery, interrupting X-ray photography will produce a high risk. If, therefore, objective information indicates a surgical operation in which interrupting X-ray photography can produce a high risk (which corresponds to "surgical operation A" in FIG. 5), it is necessary to select the first mode. Performing the following processing in step S402 makes it possible to determine whether objective information indicates a surgical operation in which interrupting X-ray photography can produce a high risk, e.g., brain surgery.

For example, the latest photography target region (a target region to be photographed next) which is written in medical care information is checked. If the photography target region is a surgical operation target region in which interrupting X-ray photography can produce a high risk, e.g., "brain", it is determined that the objective information indicates a surgical operation in which interrupting X-ray photography can produce a high risk. It is possible to perform such processing by checking whether a preset keyword (a keyword indicating a surgical operation target region in which interrupting X-ray photography can produce a high risk, e.g., "brain") is the latest photography target region written in the medical care information.

If the objective of X-ray photography to be performed is "surgical operation B" or "surgical operation C", i.e., if the objective information derived in step S402 indicates "surgical operation B" or "surgical operation C", the CPU 201 selects the second mode in step S403. The second mode is a mode for performing preset operation control after determining that information communication from the operation unit 110 is not normally performed. The second mode is an operation mode which attaches importance to a reduction in the exposure dose of the object 105.

Assume that a planned surgical operation like "performing surgery in accordance with a specific procedure from a specific time to a specific time in one surgical operation" (which corresponds to "surgical operation B" or "surgical operation C" in FIG. 5) is to be performed while X-ray photography is performed. In this case, it is necessary to perform X-ray photography in accordance with conditions based on such a plan. In this case, therefore, it is necessary to select the second mode. Note that performing the following processing in step S402 makes it possible to determine whether objective information indicates a planned surgical operation.

For example, it is checked whether a plan (schedule) item concerning the next surgical operation is written in the latest reservation information written in medical care information. If such an item is written, it is determined that the objective information indicates a planned surgical operation.

If the objective of X-ray photography to be performed is "surgical operation D" or "examination E", i.e., if the objective information derived in step S402 is "surgical operation D" or "examination E", the CPU 201 selects the third mode in step S403. The third mode is a mode for performing ABC (Auto Brightness Control) control after it is determined that information communication from the operation unit 110 is not normally performed. Like the second mode, the third mode is an operation mode which attaches importance to a reduction in the exposure dose of the object 105.

Assume that an operation to be performed is not a planned surgical operation like that described above and is a surgical operation or examination on a region, e.g., a digestive organ system which is not so important as the brain (which corresponds to "surgical operation D" or "examination E" in FIG. 5), it is desired to perform ABC control. In this case, therefore, it is necessary to select the third mode. Note that performing the following processing in step S402 can determine whether the object information indicates an operation which is not a planned surgical operation like that described above and is a surgical operation or examination on a region which is not so important as the brain, e.g., a digestive organ system.

For example, the latest photography target region (the target region to be photographed next) written in the medical care information is checked. If the photography target region is a region such as "stomach" which is not so important as the brain, it is determined that the objective information is not a planned surgical operation like that described above and a surgical operation or examination on a region, e.g., a digestive organ system which is not so important as the brain. It is possible to perform such processing by performing search processing of checking whether a preset keyword (a keyword indicating a region such as "stomach" which is not so important as the brain) is the latest photography target region written in the medical care information.

If the objective of X-ray photography is "examination F", i.e., if the objective information derived in step S402 is "examination F", the CPU 201 selects the fourth mode in step S403. The fourth mode is a mode for stopping X-ray photography when it is determined that information communication from the operation unit 110 is not normally performed. The fourth mode is a mode which attaches importance to the reliability of the apparatus when, for example, continuing irradiation in a state in which operation instruction information from the operation unit 110 cannot be communicated will produce a high risk.

If, for example, the latest reservation information written in medical care information is checked, and the word "surgical operation" is not written in the information, it is determined that the objective information indicates "examination". It is possible to perform this processing by performing search processing of checking whether a preset keyword (a keyword indicating "surgical operation") is written in the latest reservation information.

Note that these operation modes are used when information communication from the operation unit 110 is not normally performed, but are not used during normal operation.

Referring to FIG. 5, the number of selectable modes is four. However, the number and contents of modes are not limited to those described above, and can be changed as needed in accordance with the environment to which the X-ray image diagnosis apparatus is applied.

The above processing for deriving objective information from medical care information is merely an example. Various kinds of processing for this purpose are conceivable.

Figure 6:
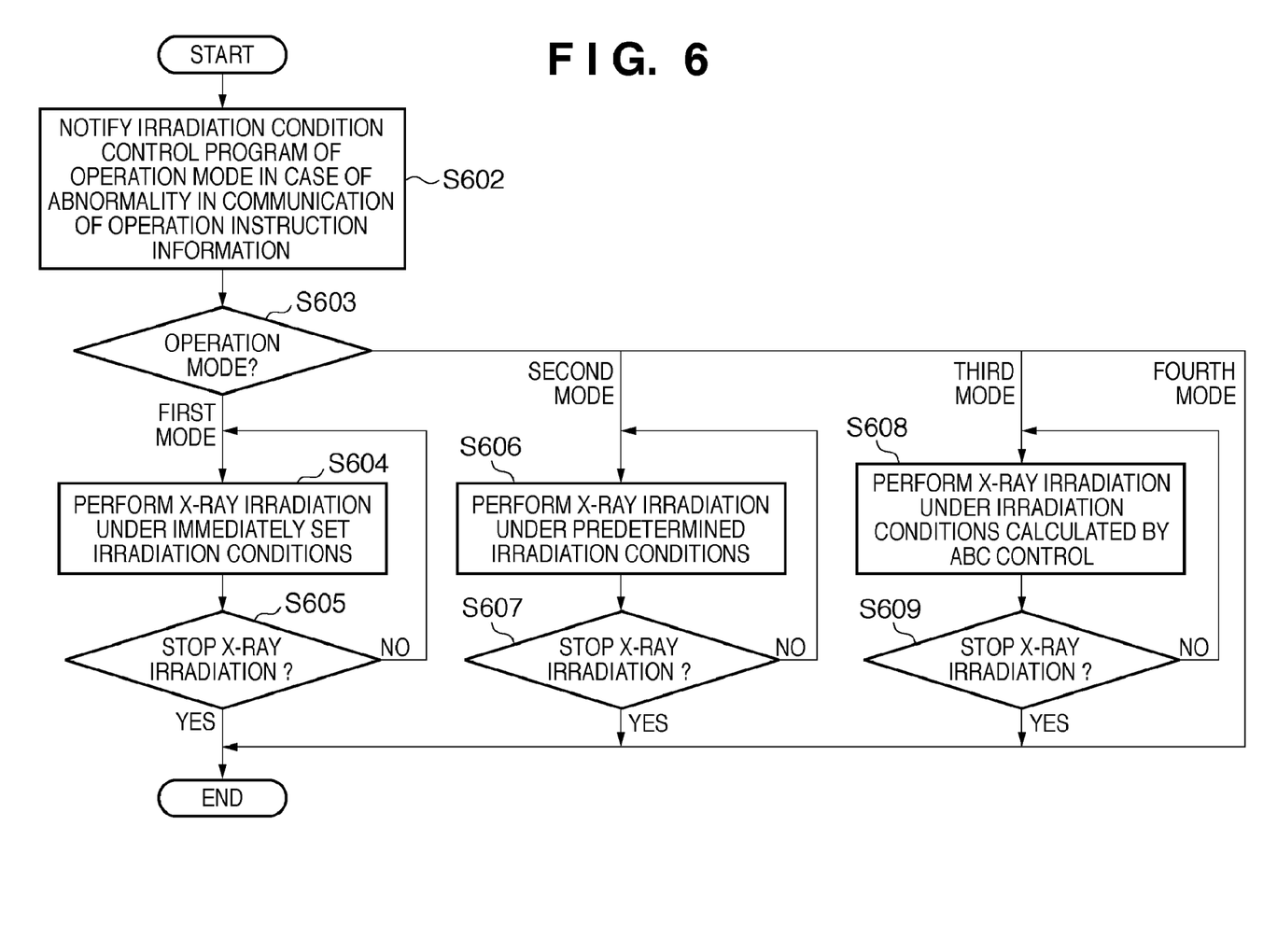
FIG. 6 is a flowchart showing the details of processing in step S307.

The details of processing in step S307 will be described next with reference to FIG. 6. FIG. 6 is a flowchart showing the details of the processing in step S307.

First of all, in step S602, the CPU 201 notifies the irradiation condition control program 206 of the operation mode determined in step S303.

If the operation mode determined in step S303 is the first mode, the process advances to step S604 via step S603. If the operation mode determined in step S303 is the second mode, the process advances to step S606 via step S603. If the operation mode determined in step S303 is the third mode, the process advances to step S608 via step S603. If the operation mode determined in step S303 is the fourth mode, the CPU 201 terminates this processing via step S603. That is, the CPU 201 immediately interrupts X-ray photography.

In step S604, the CPU 201 continues the operation control on the X-ray controller 108 and the image reading unit 111, which has been performed immediately before it is determined that information communication from the operation unit 110 is not normally performed, after the determination. That is, X-ray irradiation is performed under the respective irradiation conditions (a tube current, tube voltage, frame rate, and the like) which have been set immediately before it is determined that information communication from the operation unit 110 is not normally performed, without changing them.

In step S605, the CPU 201 checks whether an instruction to stop X-ray irradiation is input. For example, the CPU 201 checks whether the operator has pressed the emergency stop button provided in the system different from that of the operation unit 110. Upon determining as a result of the check that an instruction to stop X-ray irradiation is input, the CPU 201 interrupts X-ray irradiation by terminating this processing. If an instruction to stop X-ray irradiation is not input, the process returns to step S604.

In step S606, the CPU 201 performs operation control so as to perform X-ray irradiation based on preset various irradiation conditions.

In step S607, the CPU 201 checks whether an instruction to stop X-ray irradiation is input. For example, the CPU 201 checks whether the operator has pressed the emergency stop button provided in the system different from that of the operation unit 110. Upon determining as a result of this check that an instruction to stop X-ray irradiation is input, the CPU 201 interrupts X-ray irradiation by terminating this processing. If an instruction to stop X-ray irradiation is not input, the process returns to step S606.

In step S608, the CPU 201 turns on setting information for ABC control, and performs operation control so as to perform X-ray irradiation based on various irradiation conditions determined by ABC control.

In step S609, the CPU 201 checks whether an instruction to stop X-ray irradiation is input. For example, the CPU 201 checks whether the operator has pressed the emergency stop button provided in the system different from that of the operation unit 110. Upon determining as a result of this check that an instruction to stop X-ray irradiation is input, the CPU 201 interrupts X-ray irradiation by terminating this processing. If an instruction to stop X-ray irradiation is not input, the process returns to step S608.

Although FIG. 1 shows the X-ray medical care information management unit 114 as a processing unit independent of the system controller 109, the system controller 109 may incorporate the X-ray medical care information management unit 114. Alternatively, an apparatus different from the X-ray image diagnosis apparatus may include the X-ray medical care information management unit 114, and the X-ray image diagnosis apparatus may acquire information in the X-ray medical care information management unit 114 via a network.

Second Embodiment

The first embodiment derives objective information indicating the objective of X-ray photography to be performed for the object 105 based on the medial care information of the object 105 managed by the X-ray medical care information management unit 114. However, an arrangement for acquiring objective information is not limited to this. It suffices to directly input objective information via the operation unit 110.

The second embodiment is the same as the first embodiment except that objective information is directly input by using an operation unit 110.

Figure 7:
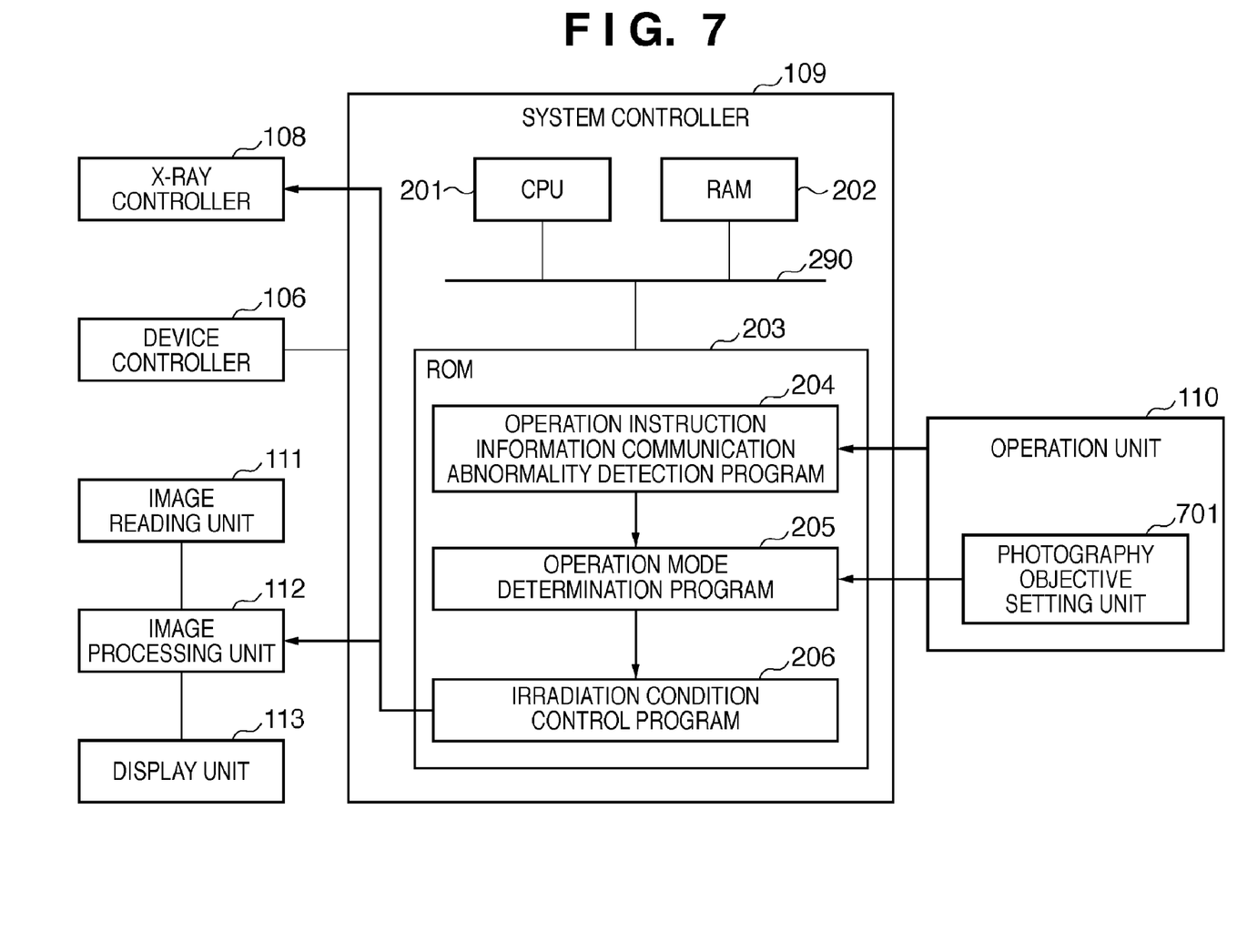
FIG. 7 is a block diagram showing an example of the arrangement of a system controller 109.

FIG. 7 is a block diagram showing an example of the arrangement of a system controller 109. The second embodiment differs from the first embodiment only in that the operation unit 110 is provided with a photography objective setting unit 701 for inputting the objective of X-ray photography to be performed.

A doctor or technician who is an operator inputs objective information indicating the objective of X-ray photography before X-ray photography. As described in the first embodiment, such objective information indicates, for example, one of surgical operations A to D, examination E, and examination F.

Upon performing an operation mode determination program 205, a CPU 201 acquires this directly input objective information. Operation performed after the acquisition of objective information is the same as that in the first embodiment.

That is, the second embodiment is the same as the first embodiment except for the acquisition form of objective information.

Processing performed by the X-ray image diagnosis apparatus according to the second embodiment basically complies with the flowchart shown in FIG. 3 but differs from it only in processing in step S303.

Figure 8:
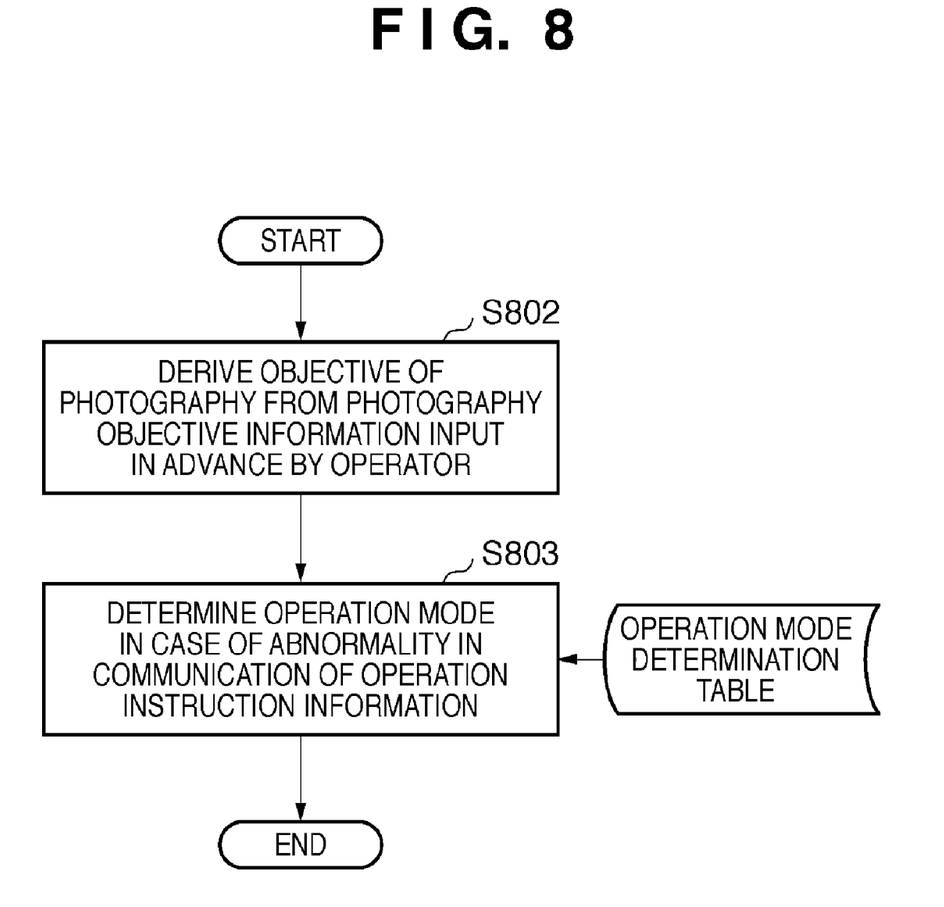
FIG. 8 is a flowchart showing the details of processing in step S303 performed in the second embodiment of the present invention.

FIG. 8 is a flowchart showing the details of processing in step S303 performed in this embodiment.

First of all, in step S802, the CPU 201 performs the operation mode determination program 205. With this operation, the CPU 201 acquires "objective information indicating the objective of X-ray photography to be performed for an object 105" input by using the photography objective setting unit 701.

Subsequently, in step S803, the CPU 201 refers to the table (operation mode determination table) exemplified in FIG. 5. In step S802, the CPU 201 determines an operation mode corresponding to the acquired objective information. The processing in this step is the same as that in step S403 described above.

Although the photography objective setting unit 701 has been described as part of the operation unit 110, the photography objective setting unit 701 may be independent of the operation unit 110.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-155886 filed Jun. 13, 2008, which is hereby incorporated by reference herein in its entirety.

What is claimed is:

1. An X-ray image diagnosis apparatus comprising an operation unit configured to input an instruction concerning X-ray photography, an X-ray photography unit configured to perform X-ray photography, and a controller configured to perform operation control on said X-ray photography unit based on control information input by said operation unit, said controller comprising a unit configured to acquire objective information indicating an objective of performing X-ray photography before X-ray photography is performed, a setting unit configured to set an X-ray photography mode corresponding to the objective information, a determination unit configured to determine whether information communication from said operation unit is normal, after said X-ray photography unit starts X-ray photography, and a control unit configured to perform operation control on said X-ray photography unit in accordance with an X-ray photography mode set by said setting unit, when said determination unit determines that the information communication is not normal.

2. The apparatus according to claim 1, wherein the objective information has been already input, or is derived from information associated with a medical care of an object to be subjected to X-ray photography.

3. The apparatus according to claim 1, wherein said setting unit sets, in accordance with the objective information, one of a first mode for continuing operation control on said X-ray photography unit, which has been performed immediately before said determination unit determines that the information communication is not normal, after said determination unit determines that the information communication is not normal, a second mode for performing preset operation control after said determination unit determines that the information communication is not normal, a third mode for performing auto brightness control after said determination unit determines that the information communication is not normal, and a fourth mode for stopping X-ray photography performed by said X-ray photography unit after said determination unit determines that the information communication is not normal.

4. A control method for an X-ray image diagnosis apparatus including an operation unit configured to input an instruction concerning X-ray photography, an X-ray photography unit configured to perform X-ray photography, and a controller configured to perform operation control on the X-ray photography unit based on control information input by the operation unit, wherein the controller performs a step of acquiring objective information indicating an objective of performing X-ray photography before X-ray photography is performed, a setting step of setting an X-ray photography mode corresponding to the objective information, a determination step of determining whether information communication from the operation unit is normal, after the X-ray photography unit starts X-ray photography, and a control step of performing operation control on the X-ray photography unit in accordance with an X-ray photography mode set in the setting step, when it is determined in the determination step that the information communication is not normal.

* * * * *